US011166803B2

(12) United States Patent
McGowan et al.

(10) Patent No.: US 11,166,803 B2
(45) Date of Patent: Nov. 9, 2021

(54) EMBOLI-CAPTURING CENTERING DEVICE

(71) Applicants: Boston Scientific Scimed, Inc., Maple Grove, MN (US); Mayo Foundation for Medical Education and Research, Rochester, MN (US)

(72) Inventors: Roger W. McGowan, Ostego, MN (US); Alexander J. Wiedmann, Columbia Heights, MN (US); Jennifer Reinhart, St. Paul, MN (US); Patrick A. Haverkost, Corcoran, MN (US); Timothy A. Ostroot, Cokato, MN (US); Gurpreet S. Sandhu, Rochester, MN (US); Daniel B. Spoon, Rochester, MN (US); Brandon J. Tefft, Rochester, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 181 days.

(21) Appl. No.: 15/945,040

(22) Filed: Apr. 4, 2018

(65) Prior Publication Data
US 2018/0289460 A1    Oct. 11, 2018

Related U.S. Application Data

(60) Provisional application No. 62/481,729, filed on Apr. 5, 2017.

(51) Int. Cl.
*A61F 2/01*    (2006.01)
*A61M 25/09*    (2006.01)

(52) U.S. Cl.
CPC ............ *A61F 2/0103* (2020.05); *A61F 2/013* (2013.01); *A61F 2/0105* (2020.05); *A61F 2/011* (2020.05);
(Continued)

(58) Field of Classification Search
CPC .... A61F 2/01; A61F 2/013; A61F 2/06; A61F 2002/011; A61F 2002/015;
(Continued)

(56) References Cited

U.S. PATENT DOCUMENTS

| 5,662,671 | A | 9/1997 | Barbut et al. | |
|---|---|---|---|---|
| 6,171,328 | B1 * | 1/2001 | Addis | A61F 2/013 606/200 |
| 6,361,545 | B1 * | 3/2002 | Macoviak | A61B 17/221 606/200 |
| 6,692,512 | B2 | 2/2004 | Jang | |

(Continued)

FOREIGN PATENT DOCUMENTS

| JP | 2002527157 A | 8/2002 |
|---|---|---|
| WO | 2013037505 A1 | 3/2013 |

(Continued)

OTHER PUBLICATIONS

Flare. (n.d.) American Heritage® Dictionary of the English Language, Fifth Edition. (2011). Retrieved Aug. 10, 2020 from https://www.thefreedictionary.com/flare (Year: 2011).*

(Continued)

*Primary Examiner* — Kathleen S Holwerda
*Assistant Examiner* — Kankindi Rwego
(74) *Attorney, Agent, or Firm* — Kacvinsky Daisak Bluni PLLC (57) ABSTRACT

In some aspects, the present disclosure pertains to self-expanding emboli-capturing centering devices for centering a medical instrument in a conduit within a patient. The centering devices comprise (a) an elongate shaft, (b) a self-expanding centering member having an open distal end and an inner surface forming a central lumen with a flared distal portion, the centering member being configured such that a fluid flowing in a distal-to-proximal direction that is received by the open distal end flows proximally along the flared distal portion of the central lumen before exiting the central lumen through one or more openings in a proximal (Continued)

portion of the centering member, and (c) a filter material configured to filter the fluid received by the open distal end of the centering member. Other aspects of the present disclosure pertain to systems and methods employing such centering devices.

20 Claims, 6 Drawing Sheets

(52) U.S. Cl.
CPC . *A61F 2002/016* (2013.01); *A61F 2220/0075* (2013.01); *A61F 2230/0067* (2013.01); *A61F 2230/0086* (2013.01); *A61F 2250/0024* (2013.01); *A61M 25/09* (2013.01)

(58) Field of Classification Search
CPC .......... A61F 2002/016; A61F 2002/018; A61F 2002/068; A61F 2/24; A61F 2/2427; A61F 2/95; A61F 2/954; A61F 2/958; A61F 2/962; A61F 2/966; A61F 2/97; A61F 2/243; A61F 2/2433; A61F 2/2436; A61F 2/2439; A61F 2002/9583; A61F 2002/9586; A61F 2002/9623; A61F 2002/9665; A61F 2/12168; A61M 25/09; A61M 25/0904; A61M 25/0067; A61M 25/0068; A61M 25/0069; A61M 25/007; A61M 25/0071; A61M 25/0074; A61M 25/0125; A61B 17/12177; A61B 17/12131; A61B 17/1204; A61B 17/12109; A61B 2017/00243; A61B 2017/22068
USPC .......................................................... 606/200
See application file for complete search history.

(56) References Cited

U.S. PATENT DOCUMENTS

| | | |
|---|---|---|
| 7,232,462 B2 | 6/2007 | Schaeffer |
| 8,845,583 B2 | 9/2014 | Boyle et al. |
| 2002/0049468 A1* | 4/2002 | Streeter ............... A61F 2/01 606/200 |
| 2002/0143361 A1 | 10/2002 | Douk et al. |
| 2002/0161394 A1 | 10/2002 | Macoviak et al. |
| 2002/0169176 A1 | 11/2002 | Elder et al. |
| 2002/0173819 A1 | 11/2002 | Leeflang et al. |
| 2005/0096734 A1 | 5/2005 | Majercak et al. |
| 2005/0124969 A1 | 6/2005 | Fitzgerald et al. |
| 2010/0076482 A1* | 3/2010 | Shu ..................... A61F 2/01 606/200 |
| 2010/0217304 A1 | 8/2010 | Angel et al. |
| 2012/0059309 A1 | 3/2012 | Di Palma et al. |
| 2012/0116351 A1 | 5/2012 | Chomas et al. |
| 2013/0096606 A1* | 4/2013 | Bruchman ............ A61F 2/013 606/200 |
| 2014/0277096 A1* | 9/2014 | Richter ............ A61B 17/12109 606/200 |
| 2016/0158006 A1 | 6/2016 | Sandhu et al. |
| 2016/0193028 A1 | 7/2016 | Fifer et al. |
| 2019/0000604 A1* | 1/2019 | Eli ..................... A61F 2/01 |

FOREIGN PATENT DOCUMENTS

| | | |
|---|---|---|
| WO | 2013166049 A1 | 11/2013 |
| WO | 2014169176 | 10/2014 |
| WO | 2015013238 | 1/2015 |

OTHER PUBLICATIONS

International Search Report and Written Opinion dated Jun. 15, 2018, for PCT/US2018/026004 (11 pages).

* cited by examiner

EMBOLI-CAPTURING CENTERING DEVICE

STATEMENT OF RELATED APPLICATION

This application claims the benefit of U.S. Provisional Application Ser. No. 62/481,729, filed Apr. 5, 2017 and entitled "EMBOLI-CAPTURING CENTERING DEVICE", which is hereby incorporated by reference in its entirety.

FIELD

The present disclosure relates to devices and methods for cardiovascular treatment and diagnosis. For example, the present disclosure relates to devices and methods by which a catheter can align itself with a blood flow stream to thereby assist the advancement of a guidewire or other elongate device from the catheter through an orifice of a heart valve, or any other passage in the body against the direction flow, while concurrently providing protection against emboli that may be generated during the course of such a procedure.

BACKGROUND

Cardiac valvular stenosis is a condition in which the heart's valves are narrowed (stenotic). With valvular stenosis, the tissues forming the valve leaflets become stiffer, narrowing the valve opening, and reducing the amount of blood that can flow through it. If the stenosis is mild, the overall cardiac output remains normal. However, when the valves can become severely stenotic, that can lead to a reduction in cardiac output and impairment of heart function.

For example, mitral valve stenosis is an abnormal narrowing of the mitral valve, resulting in a restriction of the blood flow from the left atrium to the left ventricle. The atrium heart chamber may enlarge as pressure builds up. Blood and fluid may then collect in the lung tissue (pulmonary edema), making it hard to breathe. Mitral valve stenosis can make a person severely short of breath, among other problems.

As another example, aortic valve stenosis occurs when the heart's aortic valve narrows. When the aortic valve is so obstructed, the heart has to work harder to pump blood to the body. Eventually, this extra work limits the amount of blood the heart can pump, and may weaken the heart muscle. The left atrium may enlarge as pressure builds up, and blood and fluid may then collect in the lung tissue (pulmonary edema), making it hard to breathe. Medications can ease symptoms of mild to moderate aortic valve stenosis. However, the only way to treat severe aortic valve stenosis is by surgery.

Therapies to repair or replace the aortic valve include balloon valvuloplasty (valvotomy), surgical aortic valve replacement, and transcatheter aortic valve replacement (TAVR). TAVR involves replacing the aortic valve with a prosthetic valve that is delivered via the femoral artery (transfemoral) or the left ventricular apex of the heart (transapical).

A step that can be challenging when performing a TAVR, valvuloplasty, or hemodynamic study on a stenotic aortic valve is to gain access to the left ventricle through retrograde crossing of a severely stenotic aortic valve with a guidewire, catheter, or other elongate medical device. The valve is also often highly calcified. The current practice can involve repeatedly probing of the stenotic valve with the guide wire until the orifice is penetrated. Prolonged probing can increase the risk of dislodging small amounts of calcified debris and atheroma from the valve surface and can lead to strokes.

SUMMARY

This disclosure provides devices, systems and methods for the treatment of heart conditions such as valvular stenosis. For example, this disclosure provides devices, systems and methods by which a guide catheter can align itself with a blood flow stream to thereby assist with the advancement of guidewire or other elongate device from the guide catheter, against the direction of blood flow, through a heart valve or other orifice, while at the same time decreasing the risks of unintended embolization arising from the procedure.

The devices and methods provided herein are adapted to save time and expense during cardiac catheterization procedures by aligning a guide catheter with a valve orifice capture emboli that may be released during the course of such procedures. Consequently, the devices and methods provided herein may, for example, reduce overall costs of such procedures, reduce radiation exposure for patients and physicians during such procedures, and reduce the risk of thromboembolic strokes during such procedures. The devices and methods can be used for TAVR procedures as well as for other surgical procedures and diagnostic investigations where there is a need to cross an aortic valve. In addition to treating aortic stenosis, the devices and methods provided herein have applications for perivalvular mitral valve leaks and any other fistulas and openings where there is a need to find a fluid flow and to cross against the fluid flow.

In some general aspects, this disclosure features self-expanding emboli-capturing centering devices for centering a medical instrument in a conduit within a patient. The emboli-capturing centering devices comprise: (a) an elongate shaft; (b) a self-expanding centering member having (i) a flared distal portion having open distal end, (ii) a proximal portion that is attached to the elongate shaft, (iii) an outer surface, and (iv) an inner surface forming a central lumen having a flared distal portion, the centering member being configured such that a fluid flowing in a distal-to-proximal direction that is received by the open distal end of the centering member flows proximally along the flared distal portion of the lumen before exiting the central lumen through one or more openings in the proximal portion of the centering member; and (c) a filter material configured to filter the fluid received by the open distal end of the centering member.

In some embodiments, which may be used in conjunction with the above aspects, the centering member may comprise a flared frame and a covering material disposed over a distal portion of the flared frame, the covering material configured to block passage of blood through the covering material.

In some embodiments, which may be used in conjunction with any of the above aspects and embodiments, the flared frame may comprise a plurality of petal-shaped frame segments.

In some embodiments, which may be used in conjunction with any of the above aspects and embodiments, the filter material may be positioned over the one or more openings in the proximal portion of the centering member.

In some embodiments, which may be used in conjunction with any of the above aspects and embodiments, the filter material is positioned downstream of the one or more openings in the proximal portion of the centering member.

In some embodiments, which may be used in conjunction with any of the above aspects and embodiments, the filter material may be positioned downstream of the one or more openings in the proximal portion of the centering member, and the filter material may extend from a distal end of the centering member, fold over and proximally wrap around the outer surface of the centering member, and attach to the device at a position proximal to the one or more openings in the proximal portion of the centering member. In certain of these embodiments, the centering member may comprise a flared frame and a covering material disposed over a distal portion of the flared frame that is configured to block passage of blood through the covering material in which case, for example, the filter material may be an extension of the covering material (e.g., where pores are formed in the covering material) or the filter material may be a material that is distinct from the covering material.

In some embodiments, which may be used in conjunction with any of the above aspects and embodiments, the filter material may positioned downstream of the one or more openings in the proximal portion of the centering member, and the device may comprise one or more filter pouches having one or more mouths that are attached to the centering member and capture the fluid exiting the one or more openings in the proximal portion of the centering member. In certain of these embodiments, the one or more filter pouches may be attached to a tether, the one or more filter pouches may be attached to a member that slides along an axis of the elongate shaft, or the one or more filter pouches may be attached to the elongate shaft.

In some embodiments, which may be used in conjunction with any of the above aspects and embodiments, the filter material may be positioned downstream of the one or more openings in the proximal portion of the centering member, and the filter material may be supported by an expandable loop structure that self-expands along with the centering member, has a diameter that is greater than that of the centering member, and is supported at a longitudinal position that is approximately the same as that of the open distal end of the centering member. In some of these embodiments, the filter material may in the form of a filter bag having a mouth that attaches to the loop and through which the elongate shaft passes at a position proximal to the centering member. In some of these embodiments, for example, (a) the expandable loop structure may be supported by one or more structural members that extend between the expandable loop structure and the distal end of the centering member or (b) the expandable loop structure may be supported by one or more structural members that extend between the expandable loop structure and the elongate shaft.

In some embodiments, which may be used in conjunction with any of the above aspects and embodiments, the filter material may be positioned downstream of the one or more openings in the proximal portion of the centering member, and the filter material may be attached to an expanding frame that is attached to the elongate shaft at a position proximal to the centering member. In certain of these embodiments, the expanding frame may be of a greater diameter than the centering member.

In other general aspects, this disclosure features systems for treating a human patient. The systems may comprise (a) a self-expanding emboli-capturing centering device in accordance with any of the above aspects and embodiments, (b) a guide catheter having a lumen, and (c) a guide wire, wherein the self-expanding emboli-capturing centering device is configured to be compressed into a low-profile configuration for advancement through the lumen of the guide catheter and to self-expand to an expanded configuration when expelled from the lumen of the guide catheter, and wherein the guide wire is configured to be advanced through a lumen of the elongate shaft of the self-expanding emboli-capturing centering device.

In other general aspects, this disclosure features methods for treating or diagnosing a human patient using such systems. The methods may comprise (a) inserting the guide catheter into a patient and directing the guide catheter to a target site within the patient; (c) causing the self-expanding emboli-capturing centering device to emerge from a distal end of the lumen of the guide catheter, wherein the self-expanding emboli-capturing centering device reconfigures from a low-profile configuration to an expanded configuration when the self-expanding emboli-capturing centering device emerges from the guide catheter lumen; and (d) causing the guidewire to emerge from a distal end of the lumen of the elongate shaft of the self-expanding emboli-capturing centering device.

Such methods may be used, for example, in any procedure where it is desirable to center the centering device on a source of fluid flow and to cause the guidewire to emerge from the centering device and to cross against the fluid flow, while at the same time providing a mechanism for capturing unintended emboli arising from the procedure.

Details of various aspects and embodiments of the invention are set forth in the description to follow and in the accompanying drawings. Other features and advantages of the invention will be apparent from the description and drawings, and from the claims.

DETAILED DESCRIPTION

This disclosure provides devices and methods by which a catheter (e.g., a guide catheter such as a 6 French guide catheter) can align itself with a blood flow stream flowing from an orifice to thereby help direct a guidewire or other elongate device transmitted from the guide catheter through the orifice, while at the same time capturing emboli that may be generated during the course of such procedures.

Figure 1:
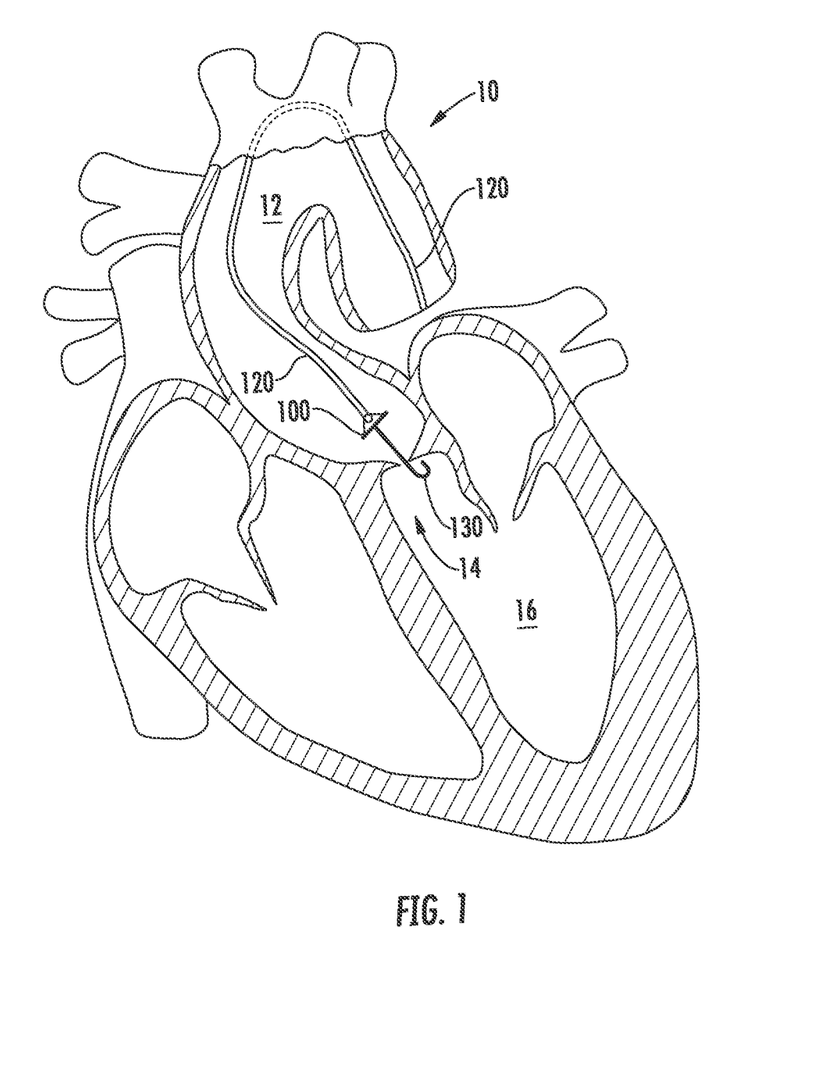
FIG. 1 is a schematic diagram of a human heart shown in partial cross-section undergoing a catheterization using an emboli-capturing centering device to transmit a guidewire through an aortic valve orifice, in accordance with some embodiments provided herein.

With reference to FIG. 1, a schematic diagram is provided of a human heart 10 shown in partial cross-section undergoing a catheterization using a guide catheter 120. The guide catheter 120 is depicted in an aortic arch 12 for the purpose of transmitting a guidewire 130 through the orifice of an aortic valve 14. The blood flow in this region of heart 10 is from a left ventricle 16 to the aortic arch 12. Therefore, the guide catheter 120 is attempting to insert the guidewire 130 upstream against the blood flowing from the left ventricle 16 to the aortic arch 12.

The process of crossing a heart valve using a guidewire is performed as a step in various heart treatment and diagnostic procedures. For example, TAVR procedures, valvuloplasties, hemodynamic studies on a stenotic valve, left ventricular ablation, and other types of procedures that involve the placement of a guidewire through the orifice of a heart valve. In addition to aortic valve procedures, other applications involving the placement of a guidewire through an orifice include perivalvular mitral valve leak treatment procedures (or perivalvular aortic valve leak) and other treatment procedures involving fistulas at any site in the human heart or body.

The aortic valve 14 can be approached by the guide catheter 120 via the aortic arch 12. In some cases, the guide catheter 120 can be percutaneously inserted in a femoral artery of a patient, and directed to the patient's aorta. From the aorta, the guide catheter 120 can be directed to the aortic arch 12. In other cases, the aortic arch 12 can be accessed by the guide catheter 120 via the patient's radial artery. Other aortic arch 12 access techniques are also envisioned. While the guide catheter 120 is generally linear at its distal end portion in the depicted embodiment, in some embodiments the distal end portion of the guide catheter 120 may be angled (e.g., having a terminal angle). With the distal tip of the guide catheter 120 in a position superior to the aortic valve 14, the guidewire 130 can be ejected. The purpose of ejecting the guidewire 130 is to insert the guidewire 130 through the orifice of the aortic valve 14.

The apparatus of FIG. 1 further includes an emboli-capturing centering device 100. In some embodiments, the emboli-capturing centering device 100 is collapsible to a low-profile delivery configuration and contained within the guide catheter 120 during the insertion of the guide catheter 120 into and within the patient as described herein. When the distal tip of the guide catheter 120 reaches the target site, such as the position superior to the aortic valve 14 as shown, the emboli-capturing centering device 100 can be advanced from the guide catheter 120. In various embodiments, the emboli-capturing centering device 100 is self-expanding such that the emboli-capturing centering device 100 reconfigures itself from the low-profile delivery configuration to an expanded configuration as shown and includes a centering member having a flared shape. In some embodiments, the guidewire 130 is ejected through a lumen of the emboli-capturing centering device 100.

When the emboli-capturing centering device 100 is located in a fluid flow path, the shape of the centering member of the emboli-capturing centering device 100 causes the emboli-capturing centering device 100 to center itself in the fluid flow path. As will be described further herein, the flared shape of the centering member of the emboli-capturing centering device 100 is configured to receive or catch a jet flow of fluid (e.g., blood flowing through the orifice of the aortic valve 14 in this example).

Figure 2:
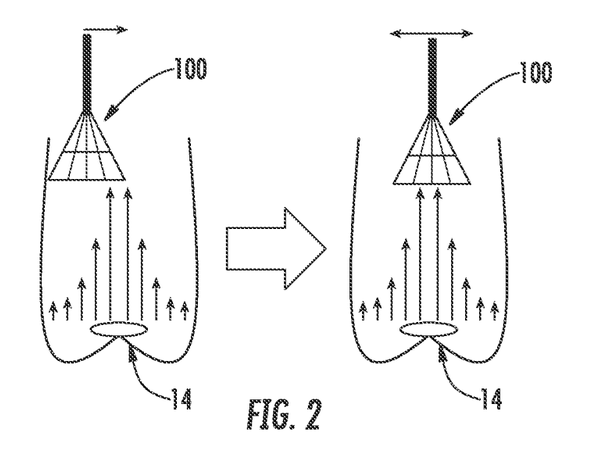
FIG. 2 is a schematic illustration showing a stenosed aortic valve and the flow gradients downstream of the same, which provide enhanced centering forces, relative to a normal aortic valve, for an emboli-capturing centering device in accordance with the present disclosure.
Figure 3:
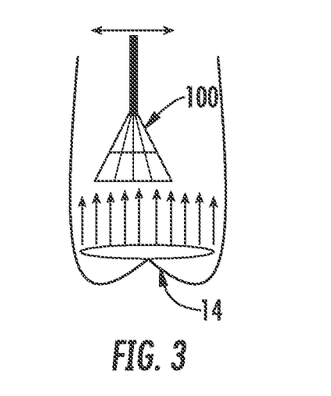
FIG. 3 is a schematic illustration showing a normal aortic valve and the flow gradients downstream of the same, which provide reduced centering forces, relative to a stenosed aortic valve, for an emboli-capturing centering device in accordance with the present disclosure.

As better seen from FIG. 2, when jet flow of blood flowing from the orifice of the aortic valve 14 contacts an interior side surface of emboli-capturing centering device 100, the impact force delivered by the jet flow of blood drives the emboli-capturing centering device 100 laterally toward the jet flow so that the jet flow of fluid is caught at or near to the center of the emboli-capturing centering device 100. The amplified effect of having a narrow jet of fluid flow, for example, emanating from a stenosed aortic valve (because the orifice of the stenosed valve is smaller for the same amount of fluid as a healthy valve), as illustrated schematically in FIG. 2, can be seen by comparison to the effect of a broad region of fluid flow, for example, emanating from a healthy aortic valve, as illustrated schematically in FIG. 3.

Since the emboli-capturing centering device 100 is located at the distal end of the guide catheter 120, when the emboli-capturing centering device 100 is centered on the fluid flow that is coming from the orifice of the aortic valve 14, the guide catheter 120 is also centered on such fluid flow. In this manner, the emboli-capturing centering device 100 causes the longitudinal axis of the guide catheter 120 to be in alignment with the orifice of the aortic valve 14. Therefore, when a guidewire 130 is ejected from guide catheter 120, the guidewire 130 is more closely aligned to a true center of the orifice of the aortic valve 14, thereby improving crossing of the guidewire 130 through the aortic valve 14.

Figure 4:
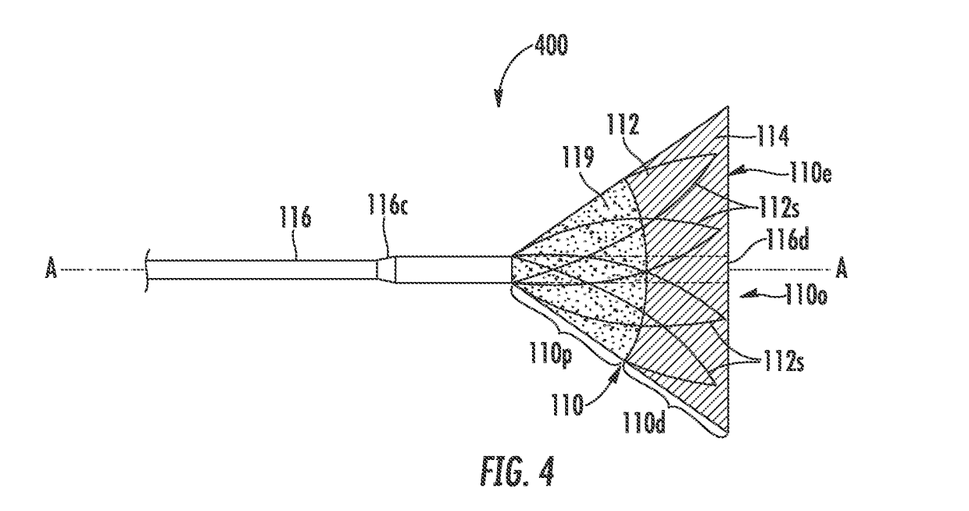
FIG. 4 is a schematic illustration of an emboli-capturing centering device in accordance with an embodiment of the present disclosure.

A more detailed view of an emboli-capturing centering device 400 having axis A is shown schematically in FIG. 4, in accordance with an embodiment of the present disclosure. The emboli-capturing centering device 400 includes (a) an elongate shaft 116 having a longitudinal axis A, a distal end 116d, and a lumen that is configured to transmit a guidewire, catheter, or other elongate device therethrough and (b) a flared centering member 110 having (i) a proximal portion 110p that is attached to the elongate shaft 116 and (ii) a distal portion 110d having an open distal end 110o, (iii) and a central axial lumen whose diameter decreases in a distal-to-proximal direction in at least the distal portion 110d of the centering member 110. In the particular embodiment shown, the centering member 110 includes a flared frame 112, formed from one or more filamentous elements. A covering material 114, which blocks passage of a fluid such as blood (e.g., formed from a non-porous material), covers the frame 112 in the distal portion 110d of the centering member 110. A filter material 119, which has openings (e.g., pores having a pore size within a range of 50-200 microns, among other possible sizes) that allow the passage of blood, except for particulates in the blood having a certain minimal size, covers the frame 112 in the proximal portion 110p of the centering member 110.

Because the covering material 114 blocks the flow of fluid, fluid that enters the central lumen of the centering member 110 via the open distal end 110o remains in the central lumen over the length of the distal portion 110d of the centering member 110 until reaching the proximal portion 110p of the centering member 110, whereupon the fluid is able to pass through openings in the filter material 119, thereby escaping from the axial lumen, and continuing to flow downstream. As a result of this design, fluid entering the axial lumen of the centering member is filtered before continuing downstream. Also as a result of the design, the centering member 110 will tend to self-center itself with a jet of fluid flowing into the axial lumen. Hence, when an emboli-capturing centering device 100 in accordance with the present disclosure is used in conjunction with a guide catheter 120 (see, e.g., FIG. 1), the centering member 110 of the emboli-capturing centering device 100 can center the catheter 120 in relation to blood flow through a narrow orifice, such as blood flow through the orifice of aortic valve 14. When the catheter 120 is centered in relation to an aortic valve 14, guidewire 130 can be advanced with an increased likelihood of successful passage through the orifice of the aortic valve 14. Moreover, blood passing through the centering member 110 is filtered to remove any particulates from the blood over a certain size (e.g., emboli may be captured by a filter material having pores ranging from 50-200 microns in size, among other possible pore sizes), including emboli released during passage of the guidewire 130 through the orifice.

Even assuming that a crossing procedure is successful with relatively few attempts, for example, because the orifice of an aortic valve 14 is crossed by a guidewire 130 on a first crossing attempt, there is still a clinical risk that emboli can become dislodged from the valve and travel downstream. This is especially problematic in the aortic arch 12, because there is an increased risk of stroke due to the close proximity of the aortic arch 12 to the carotid arteries. Moreover, candidates for TAVR will have a clinical case of aortic valve stenosis, which is often accompanied by significant calcification of the aortic valve 14, leading to increased clinical risk of dislodgment of calcified emboli from the aortic valve 14. By employing a filter material 119 in the centering member 110, emboli larger than the openings in the filter material 119 will be captured, reducing the risk of stroke.

A range of different diameters of the distal end 110e of the centering member 110 are envisioned, so as to suit different usage variations and body sizes. For example, in some embodiments the distal end 110e of the centering member 110 ranges between about 5 to 40 millimeters in diameter, about 10 to 35 millimeters in diameter, about 15 to 30 millimeters in diameter, or about 20 to 25 millimeters in diameter. Other centering member 110 diameters of the distal end 110e are also contemplated.

While the centering member 110 depicted in FIG. 4 and elsewhere herein has a substantially frusto-conical geometry, a range of flared geometries may be employed for the centering member 110 in addition to frusto-conical geometry, including a bell-shaped geometry, a frusto-pyramidal geometry (e.g., having 3, 4, 5, 6, 7, 8, 9, 10 sides or more), and so forth.

The flared frame 112, for use in conjunction with the present disclosure, may be formed from a single piece of material (e.g., in the form of a single-filament construction or a laser-cut tube that is expanded into to a desired flared shape, which is heat-set to make the flared shape the natural configuration) or formed from a plurality of frame segments 112s (e.g., thin strands, such as wires, filaments, ribbons, and so forth) that are shaped and held together, for instance by welding, adhesives, mechanical means, and so forth, to create the flared frame 112.

The frame 112 may be formed from various metals and metal alloys, including nitinol (NiTi alloy) (e.g., superelastic nitinol), stainless steel, titanium, and Elgiloy (Co—Cr—Ni Alloy), among others. The frame 112 may also be formed from various polymers.

In general, the frame 112 is collapsible to fit within the lumen of a catheter. The frame 112 can radially self-expand to a flared unconstrained configuration as shown upon deployment from the catheter. In such an example, the frame 112 may be comprised of a shape-memory material, for example, a shape memory alloy such as super-elastic nitinol (NiTi) material or a shape memory polymer.

In the specific embodiment shown in FIG. 4 (as well as FIGS. 5-9 described below), the frame 112 is constructed from a series of petal shaped frame segments 112s (e.g., three, four, five, six, seven, eight, nine, ten, or more petal shaped frame segments 112s) positioned around the device axis A. The petal shaped frame segments 112s are configured to collapse for containment within a guide catheter 120. Upon emergence from the guide catheter 120, the petal shaped frame segments 112s are configured to open up to create an overall flared shape, in particular, a generally frusto-conical shape as shown, a bell shape or other funnel shape, among others. In various embodiments, the petal shaped frame segments 112s are constructed of a shape-memory material that facilitates the collapsibility and expandability of the petals. The petal shaped frame segments 112s are formed from thin strands (e.g., wires, filaments, ribbons, etc.) of a suitable material. In various embodiments, the petal shaped frame segments 112s overlap with each other upon expansion. In such embodiments, (a) in the distal portion 110d where the covering material 114 covers the frame 112, the covering material 114 may cover roughly triangular openings and (b) in the proximal portion 110p, where the filter material 119 covers the frame 112, the filter material 119 may cover roughly triangular and quadrilateral openings between the filaments forming the petal shaped frame segments 112s.

In some embodiments, the frame 112 may include one or more visualization markers (not shown), such as radiopaque markers, bands, or radiopaque filler materials. The radiopaque markers can assist a clinician with in situ radiographic visualization of the centering member 110 so that the clinician can orient the device as desired in relation to the anatomy of the patient.

The covering material 114 employed in the embodiment shown in FIG. 4, as well as other embodiments described herein (see, e.g., FIGS. 5-9 described below), may be made of any flexible, biocompatible material capable of acting as a barrier to fluid flow (e.g., blood emerging from the orifice of a heart valve). Such covering materials can include, but are not limited to polymeric films and fabrics including polyesters such as polyethylene terephthalate, fluoropolymers such as polytetrafluoroethylene (PTFE) and expanded polytetrafluoroethylene (ePTFE), polyamides, including nylon, polyether block amides (e.g., PEBAX), chemical vapor deposited polyxylylene polymers (parylenes) including poly(p-xylylene) polymers, polysiloxanes including silicone, polyurethanes, including thermoplastic polyurethanes (TPU), such as polyether polyurethanes, polyisobutylene-polyurethanes, polyurethane-silicone copolymers, poly(vinylidene fluoride-hexafluoropropylene) (PVDF-HFP), polyisobutylene copolymers including polyisobutylene-polystyrene block copolymers such as polystyrene-polyisobutylene-polystyrene triblock copolymers (SIBS), as well as metallic films, or combinations of the foregoing materials.

The filter material 119 employed in the embodiment shown in FIG. 4, as well as other embodiments described herein (see, e.g., FIGS. 5-9 described below), may be made of any flexible, biocompatible material which can be formed or processed in a manner so as to render the material porous, thereby allowing for the filtration of particulates. Pore sizes suitable for capturing potentially harmful emboli may range, for example, from 50-200 microns, among other possible pore sizes. For example, in some embodiments, the filter material 119 may be comprised of ePTFE or another polymer, and may have ~100 um laser-drilled pores with ~50% porosity. Examples of specific materials for use as filter materials include polymers selected from those set forth immediately above for use as covering materials.

In FIG. 4, as well as other embodiments described herein (see, e.g., FIGS. 5-9 described below), the covering material 114 and the filter material 119 may be attached to structural members, including the frame 112 and the segments 112s, using a variety of techniques. For example, in some embodiments, the covering material 114 and/or the filter material 119 may be sewn to structural members. In some embodiments, the covering material 114 and/or the filter material 119 may be glued to structural members. In some embodiments, structural members may be sandwiched between layers of the covering material 114, sandwiched between layers of the filter material 119, or sandwiched between a layer of the covering material 114 and a layer of the filter material 119. In some embodiments, a combination of such attachment methods are used.

It is noted that, while the centering member 110 depicted in FIG. 4 and elsewhere herein (e.g., FIGS. 5-9) is formed from the frame 112 and the covering material 114, the centering member 110 need not be so constructed. For example, in some embodiments, the entire centering member 110 may be constructed from a flexible self-expanding material, such as an elastomeric material, which can be collapsed into a tubular structure for delivery, afterwards spring open to form a structure that has an axial lumen that is flared at its distal end to receive fluid and has apertures at its proximal end to allow that fluid to exit. In some such embodiments, the centering member 110 may include pleats and/or hinges that facilitate the collapsibility and expandability of the device.

Although the filter material 119 is employed in the proximal portion 110p of the centering device 110 in FIG. 4, in other embodiments, the filter material 119 may be placed in other portions of the emboli-capturing centering device 100.

Figure 5:
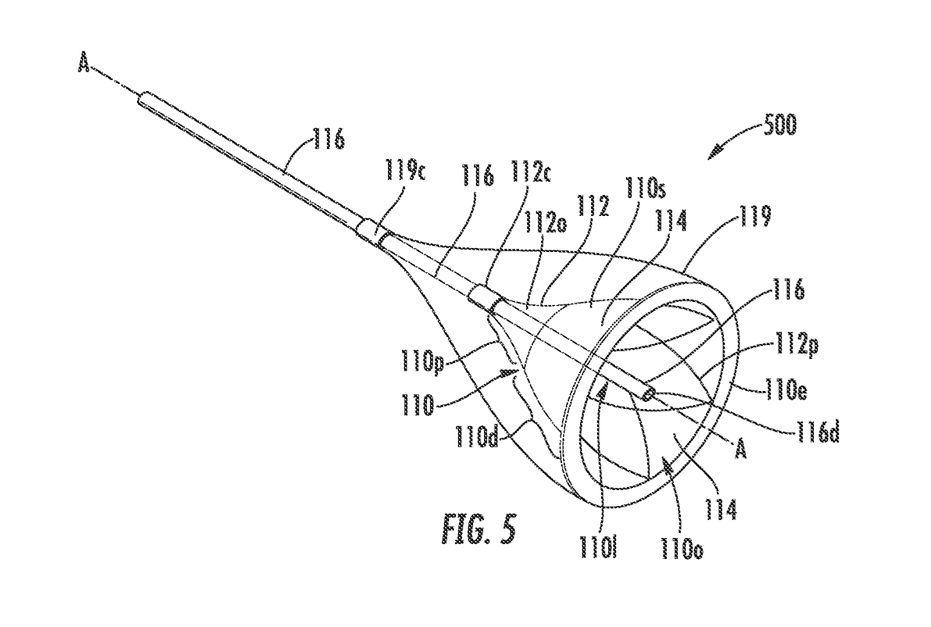
FIG. 5 is a schematic illustration of an emboli-capturing centering device in accordance with another embodiment of the present disclosure.

One embodiment of such an emboli-capturing centering device 500 is schematically illustrated FIG. 5. Analogous to FIG. 4, the emboli-capturing centering device 110 of FIG. 5 includes an elongate shaft 116 having a distal end 116d, a flared centering member 110 having a proximal portion 110p that is attached to the elongate shaft 116 and a distal portion 110d having an open distal end 110o. More specifically, in the embodiment shown, the centering member 110 includes a flared frame 112 which is attached to the elongate shaft 116 by a collar 112c, and a covering material 114, which covers the frame 112 in the distal portion 110d of the centering member 110. The centering member 110 also includes a central axial lumen 110l whose diameter decreases in a distal-to-proximal direction, at least within the distal portion 110d of the centering member 110.

Unlike FIG. 4, in the emboli-capturing centering device 500 of FIG. 5, the filter material 119 extends from a distal end 110e of the centering member 110, folding over and proximally wrapping around an outer surface 110s of the centering member 110, and attaching to the elongate shaft 116 at a position proximal to the openings between the elements of the frame 112 in the proximal portion 110p of the centering member 110. As elsewhere herein, the filter material 119 has openings that allow the passage of blood except for particulates in the blood having a certain minimal size (e.g., particulates captured by a filter material having pores ranging from 50-200 microns in size, among other possible pore sizes). In some embodiments, the filter material 119 may be an extension of the covering material 114, in which case openings may be formed in the material in those areas corresponding to the filter material 119 in order to give the material particle-filtering properties. In some embodiments, the filter material 119 may be formed of a different material than that the covering material 114 and may be attached, at the distal end 110e of the centering member 110, to the frame 112, to the covering material 114, or both.

Consequently, in the device of FIG. 5, fluid flowing in a distal-to-proximal direction that is received by the open distal end 110o of the centering member 110 flows proximally along a portion of the central lumen 110l in the distal portion 110d of the centering member 110 before exiting the central lumen 110l through the openings 112o between the elements of the frame 112 in the proximal portion 110p of the centering member 110. After passing through the openings 110o, the fluid passes through the filter material 119, thereby removing emboli of a certain minimal size that may be present (e.g., emboli captured by a filter material having pores ranging from 50-200 microns in size, among other possible pore sizes). It is noted that, under the same flow conditions and using the same filter material 119, fluid flow through the centering member 110 of FIG. 5 may be greater than fluid flow through the centering member 110 of FIG. 4, due to the substantially greater area of the filter material 119 in FIG. 5 relative to FIG. 4, through which the fluid can flow.

Various additional configurations for placement of the filter material 119 are also envisioned. For example, with reference to FIG. 6A, an emboli-capturing centering device 600a is schematically illustrated which includes an elongate shaft 116, a flared centering member 110 having a proximal portion that is attached to the elongate shaft 116 and a distal portion having an open distal end. The flared centering device 600a includes a central lumen that tapers from one diameter at the open distal end of the centering device 600a to a lesser diameter at a position proximal to the open distal end of the centering device 600a and, in the embodiment shown, includes a flared frame 112, which is attached to the elongate shaft 116, terminating at collar 112c, which marks a transition between the flared frame 112 and the elongate shaft 116. The most proximal portion of the flared frame 112 may lie parallel to the elongate shaft 116. In some embodiments, a retention collar may be provided, for example, which extends over at least some of the length of, and in some embodiments over all of the length of, the proximal portion of the flared frame 112 that lies parallel to the elongate shaft 116, thereby enhancing retention of the proximal end of the flared frame 112 to the elongate shaft 116. The flared centering device 600a further includes a covering material 114, which covers the frame 112 in the distal portion of the centering member 110.

Figure 6A:
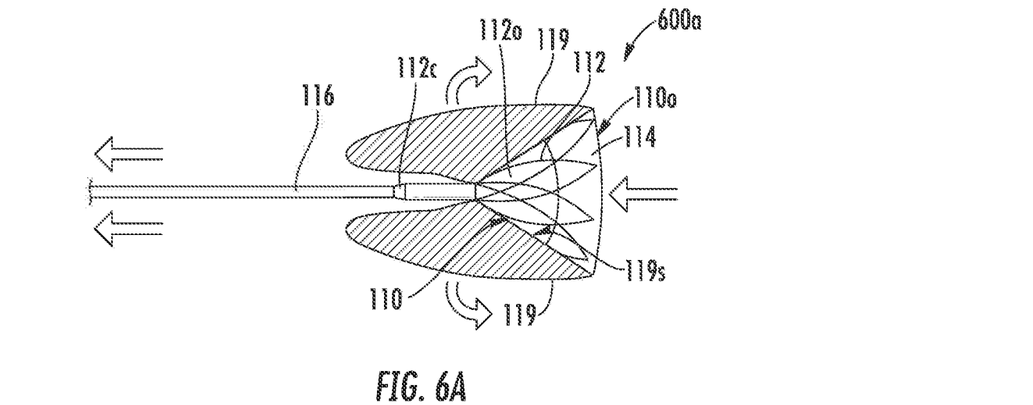
FIGS. 6A-6C are schematic illustrations of emboli-capturing centering devices in accordance with three embodiments of the present disclosure.

The filter material in FIG. 6A is in the form of one or more filter pouches 119 that are attached to the centering member 110 around the entire circumference of the centering member 110 such that fluid flowing in a distal-to-proximal direction that is received by the open distal end 110o of the centering member 110 flows proximally along a portion of the central lumen of the centering member 110 before exiting the central lumen of the centering member 110 through the openings 112o between the elements of the frame 112 and into the one or more filter pouches 119, causing the one or more pouches 119 to billow outward to a degree, as shown. Emboli of a certain minimal size that may be present (e.g., emboli that are captured by a filter material having pores ranging from 50-200 microns in size, among other possible pore sizes) are thereby removed upon passing through the filter material forming the filter pouches 119. It is noted that the one or more filter pouches 119 in FIG. 6A are shown in cross-section, with the cross-hatching representing the hollow interior of the filter pouches 119. In an embodiment where the device 600a contains a single filter pouch 119, the pouch 119 would be in the form of a hollow ring or "donut", extending 3600 about the axis of the device 600a and having a slot 119s that also extends 3600 about the axis of the device 600a and provides fluid communication between the interior or the pouch 119 and the proximal portion of the centering member 110, such that all fluid flowing exiting through the openings 112o between the elements of the frame 112 in the proximal portion of the centering member 110 will pass through the filter pouch 119 before exiting the device 600a.

Figure 6B:
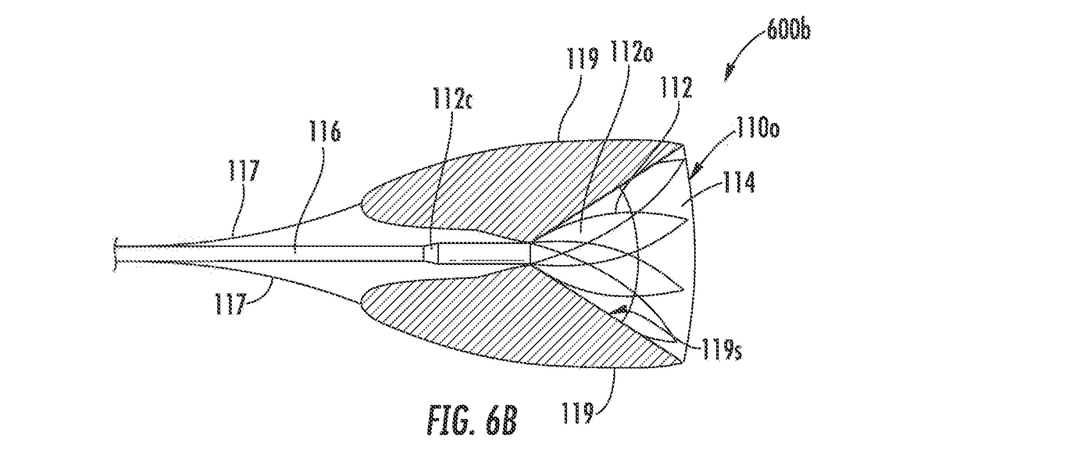
Figure 6C:
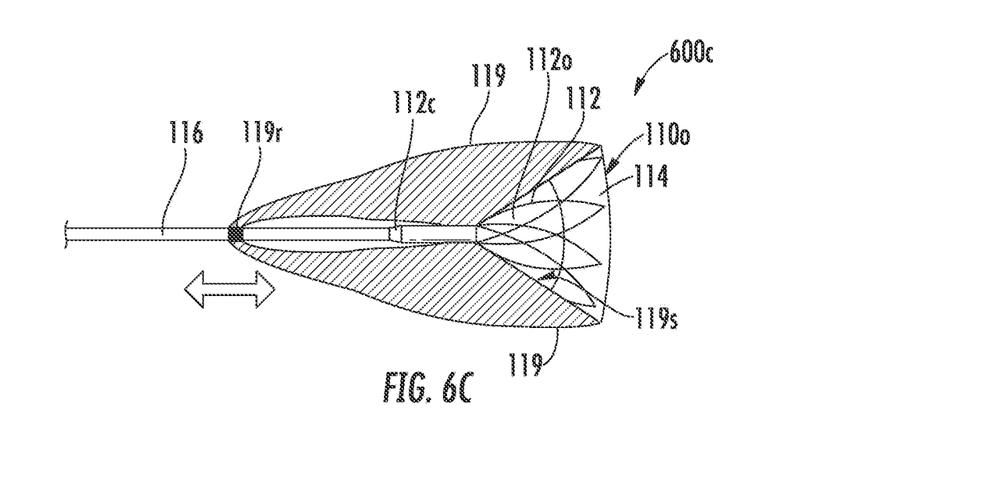

While the proximal end(s) of the one or more filter pouches 119 in FIG. 6A float(s) freely, in FIGS. 6B and 6C, the proximal ends of the of the one or more filter pouches 119 are, to a degree, constrained. In this regard, with reference to FIG. 6B, an emboli-capturing centering device 600b is shown, which is analogous to that of FIG. 6A, except one or more tethers 117 (e.g., in the form of one or more filaments) is/are attached to a proximal end of each of the one or more filter pouches 119. During a medical procedure, the tether(s) 117 extend proximally through the guide catheter (not shown) to an exterior of the body where the tether(s) 117 can be manipulated by a clinician. In this way, after a medical procedure, the one or more filter pouches 119 with captured particulate could enter the guide catheter before the centering member 110, pulled in by the tether(s) 117.

With reference to FIG. 6C, an emboli-capturing centering device 110 is shown, which is analogous to that of FIG. 6A, except that a proximal end of each of the one or more filter pouches 119 is attached to a slidable member 119r (in the form of a ring in the embodiment shown) that is slidable along a portion of the length of the elongate shaft 116. During a medical procedure, the slidable member 119r allows a guide catheter (not shown) to slide up to a proximal end of the centering member 600c (i.e., up to the collar 112c in the embodiment shown), thereby supporting the centering member 600c.

Figure 7:
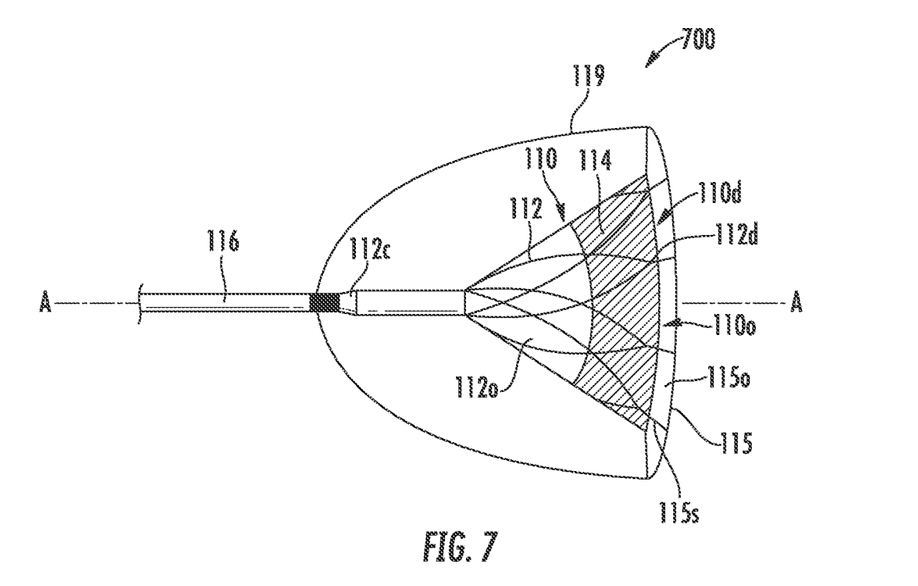
FIG. 7-9 are schematic illustrations of emboli-capturing centering devices in accordance with three further embodiments of the present disclosure.

Referring now to FIG. 7, an emboli-capturing centering device 700 is shown, which includes an elongate shaft 116, a flared centering member 110 having a proximal portion that is attached to the elongate shaft 116 and a distal portion with an open distal end 110o. The flared centering member 110 includes a central lumen that tapers from one diameter at the open distal end of the centering member 110 to a lesser diameter at a position proximal to the open distal end of the centering member 110 and, in the embodiment shown, includes (a) a flared frame 112, which is attached to the elongate shaft 116 by a collar 112c and (b) a region of covering material 114 covering the frame 112 in a distal portion 110d of the centering member 110.

The filter material in FIG. 7 is in the form of a single filter bag 119 (shown in cross-section) having a mouth that is attached to an expandable loop structure 115, which has an expanded diameter that is greater than the expanded diameter of the distal end 112d of the frame 112 (and thus has an expanded diameter that is greater than the expanded diameter of the centering member 110). The expandable loop structure 115 is supported, at a longitudinal position along an axis of the device A that is approximately the same as that of the distal end 110d of the centering member 110, by a series of support members 115s that extend between the expandable loop structure 115 and the distal end 112d of the frame 112 (at the tips of petal shaped frame segments forming frame 112 in the embodiment shown). The expandable loop structure 115 and the support members 115s in these embodiments are an extension of the frame 112 and, thus can be created in a single piece or a separate pieces, as desired. In this design, fluid flowing in a distal-to-proximal direction that is received by the open distal end 1100 of the centering member 110 will flow proximally along a portion of the central lumen of the centering member 110 before exiting the central lumen of the centering member 110 through the openings 112o of the frame 112 and into the filter bag 119. In addition, fluid flowing in a distal-to-proximal direction that is received in the openings 1150 between the loop structure 115 and the open distal end 1100 of the centering member 110 will flow proximally and directly into the filter bag 119. Emboli of a certain minimal size that may happen to be present (e.g., emboli that are captured by a filter material having pores ranging from 50-200 microns in size, among other possible pore sizes) will be removed upon passing through the filter material forming the filter bag 119.

Figure 8:
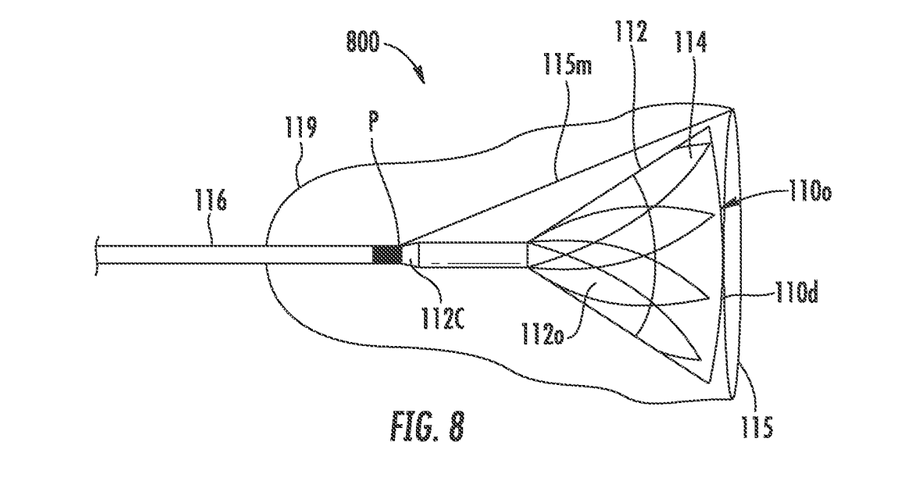

An embodiment of an emboli-capturing centering device 800 illustrated in FIG. 8 is similar to that of FIG. 7, except that the expandable loop structure 115 is supported, at a longitudinal position that is approximately the same as that of the distal end 110d of the centering member 110, by a support member 115m that extends from the expandable loop structure 115 to an attachment point P which can be on the elongate shaft 116 as shown or, for example, on a proximal portion of the centering member 110. The expandable loop 115 may be connected to the elongate shaft 116, for example, via an interface where one or more support members 115m are adjoined to one or more attachment points P by a stent-like structure (e.g., a precision cut tube interface structure, a slotted tube type structure, etc.), by a metal collar, such as a marker band or a stainless steel hypo-tube, by a wrap of material (e.g., a metallic or polymeric wire, ribbon or thread), by an adhesive joint, and so forth. As with FIG. 7, (a) fluid flowing in a distal-to-proximal direction that is received by the open distal end 110o of the centering member 110 will flow proximally along a portion of the central lumen of the centering member 110 before exiting the central lumen of the centering member 110 through the openings 112o and into the filter bag 119 and (b) fluid flowing in a distal-to-proximal direction that is received between the loop structure 115 and the open distal end 110o of the centering member 110 will flow proximally and directly into the filter bag 119. Emboli of a certain minimal size that may happen to be present (e.g., emboli that are captured by a filter material having pores ranging from 50-200 microns in size, among other possible pore sizes) will be removed upon passing through the filter material forming the filter bag 119.

Figure 9:
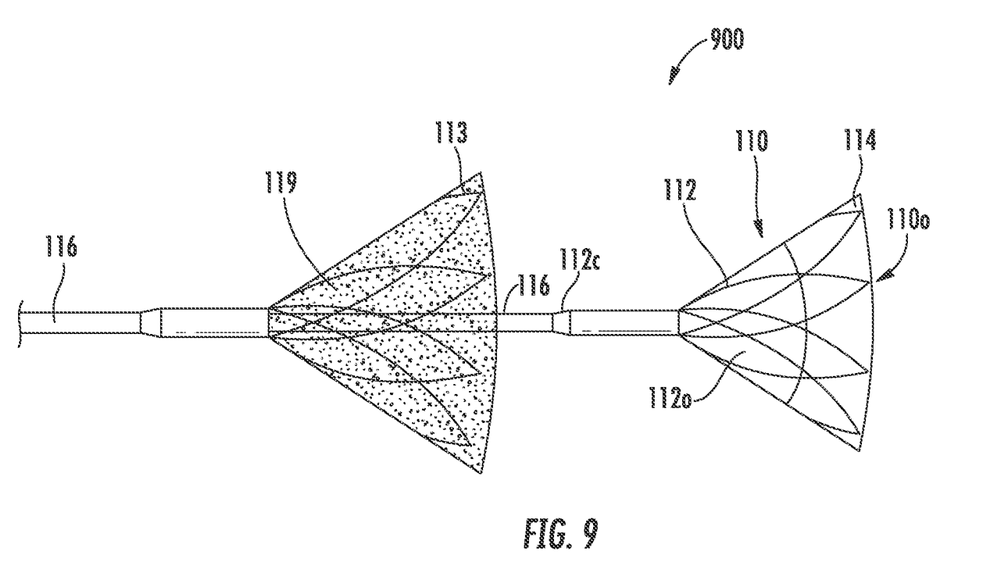

Referring now to FIG. 9, an emboli-capturing centering device 900 is shown, which includes an elongate shaft 116, a flared centering member 110 having a proximal portion that is attached to the elongate shaft 116 and a distal portion with an open distal end 110o. As in prior embodiments, the centering device 900, includes a flared frame 112 which is attached to the elongate shaft 116 and a region of covering material 114 covering the frame 112 in a distal portion of the centering member 110. The filter material 119 in FIG. 9, however, is attached to a frame 113 lying proximal the frame 112. Although the frame 113 is of a design analogous to that of frame 112 in FIG. 9, this is by no means required. In certain embodiments, a diameter of the frame 113 may be greater than a diameter of the frame 112, in order to enhance embolic protection provided by the device 900. For example, the diameter of the frame 113 may range from 50% to 200% of diameter of the frame 112. In this design, fluid flowing in a distal-to-proximal direction that is received by the open distal end 110*o* of the centering member 110 will flow proximally along a portion of the central lumen of the centering member 110 before exiting the central lumen of the centering member 110 through the openings 112*o*. As the fluid exiting the openings 112*o* continues downstream, at least a portion of this fluid will flow through the filter material 119, capturing emboli of a certain minimal size (e.g., emboli that are captured by a filter material having pores ranging from 50-200 microns in size, among other possible pore sizes) that may happen to be present.

It should be understood that one or more of the features described in reference to any one embodiment described herein may be combined with one or more of the features of other embodiments provided herein. That is, various features described herein can be mixed and matched to create hybrid designs, and such hybrid designs are within the scope of this disclosure.

As previously indicated, devices in accordance with the present disclosure are useful in advancing a guidewire or other elongate device from a catheter through an orifice (such as a heart valve) where a fluid is flowing in a counter direction to the direction the guidewire is being advanced, while at the same time filtering emboli that may be generated during the procedure. In a typical procedure, a guide catheter is inserted into a patient by a clinician. In some cases, the insertion may be percutaneous. In some cases, the insertion may be through a natural body orifice or channel. A self-expanding emboli-capturing centering device in accordance with the present disclosure can be contained in a low profile within a lumen of the catheter, and the guidewire can be advanced through a lumen in the self-expanding emboli-capturing centering device.

In use, a distal end of the guide catheter is directed to the target site within the body of the patient. Visualization systems such as x-ray fluoroscopy, MRI, or ultrasound can be utilized to assist the clinician with directing the guide catheter within the patient as desired. Once the distal end of the guide catheter is located at a desired site within the patient's body, the clinician can deploy the emboli-capturing centering device from the distal end of the guide catheter. As the centering member of the emboli-capturing centering device emerges from the confines of the guide catheter lumen, the centering member can self-expand to a flared shape as described herein. With the self-expanding emboli-capturing centering device supported by the guide catheter in the flow path of a fluid (such as blood flow from an orifice of a heart valve), the centering member will receive at least a portion of the fluid that is flowing toward the distal tip of the guide catheter. The impact of the fluid on the inner surface of the centering member will cause the centering member to move laterally so as to center itself on the fluid flow. When the fluid flow is from an orifice, the lateral movement of the centering member will cause the centering member be centered in relation to the orifice. With the axis of the elongate shaft of the self-expanding emboli-capturing centering device centered on the orifice, the clinician can eject the guidewire from the lumen of the elongate shaft. The guidewire will emerge from the lumen and be in alignment with the orifice. As such, the guidewire can be advanced through the orifice by the clinician.

The invention claimed is:

1. An emboli-capturing centering device for centering a medical instrument in a conduit within a patient with respect to a jet flow of fluid flowing through a restricted orifice within the patient narrower than the conduit and distal to the emboli-capturing centering device, the emboli-capturing centering device comprising:
an elongate shaft;
a flared centering member having a proximal end attached to the shaft, an open distal end, and an inner surface forming an axial lumen having a flared distal portion; and
a flared filter material separate from the flared centering member and configured to filter the fluid received by the open distal end of the centering member;
wherein:
the axial lumen has a diameter which decreases in a distal-to-proximal direction;
the centering member and inner surface thereof are dimensioned and configured such that the jet flow of fluid flowing in a distal-to-proximal direction that is received by the open distal end of the centering member contacts the inner surface of the centering member and flows proximally along the decreasing diameter of the axial lumen of the centering member to laterally shift the centering member to center the axial lumen of the centering member with respect to the orifice; and
the filter material is flared outwardly, from the location at which the proximal end of the flared centering member is attached to the shaft, in a direction towards the distal end of the flared centering member.

2. The emboli-capturing centering device of claim 1, wherein the centering member comprises a flared frame.

3. The emboli-capturing centering device of claim 2, further comprising a covering material disposed over a distal portion of the flared frame and configured to block passage of blood through the covering material and the distal portion of the centering member to center the axial lumen of the centering member with respect to the orifice.

4. The emboli-capturing centering device of claim 3, wherein the covering material is flared outwardly in a distal direction along the centering member.

5. The emboli-capturing centering device of claim 2, wherein the filter material is in a proximal portion of the flared frame.

6. The emboli-capturing centering device of claim 2, wherein the filter material is attached to a structural member of the frame.

7. The emboli-capturing centering device of claim 1, wherein the centering member comprises a plurality of petal-shaped frame segments.

8. The emboli-capturing centering device of claim 1, wherein the filter material covers a proximal portion of the centering member adjacent the location at which the centering member is attached to the shaft.

9. The emboli-capturing centering device of claim 8, wherein the filter material covers openings in the proximal portion of the centering member.

10. The emboli-capturing centering device of claim 1, further comprising a covering material disposed over the centering member and configured to block passage of blood through the covering material and the distal portion of the centering member to center the axial lumen of the centering member with respect to the orifice, wherein fluid flows through the filter member proximal to the covering member.

11. The emboli-capturing centering device of claim 10, wherein the filter material flares outwardly from a proximal end thereof, at the location at which the proximal end of the flared centering member is attached to the shaft, to a distal end thereof, and the covering material flares outwardly from the distal end of the filter material to the distal end of the centering member.

12. The emboli-capturing centering device of claim 1, wherein the centering member has a frusto-conical geometry.

13. The emboli-capturing centering device of claim 1, wherein the filter material is in a proximal portion of the centering member adjacent the location at which the centering member is attached to the shaft and flares outwardly therefrom in a direction towards the distal end of the centering member.

14. The emboli-capturing centering device of claim 1, wherein the centering member is constructed from a flexible self-expanding material which can be collapsed for delivery.

15. A system comprising:
  (a) an emboli-capturing centering device comprising: (i) an elongate shaft; (ii) a flared centering member having an open distal end, a proximal end attached to the shaft, and an inner surface forming an axial lumen whose diameter decreases in a distal-to-proximal direction; and (iii) a flared filter material separate from the flared centering member;
  (b) a guide catheter having a lumen; and
  (c) a guide wire;
  wherein:
  the flared centering member and inner surface thereof are dimensioned and configured such that a fluid flowing in a distal-to-proximal direction from an orifice distal to the centering device that is received by the open distal end of the centering member contacts the inner surface of the centering member and flows proximally along the decreasing diameter of the axial lumen of the centering member to laterally shift the centering member to center the axial lumen of the centering member with respect to the orifice;
  the filter material is flared outwardly, in a distal direction, from the location at which the proximal end of the flared centering member is attached to the shaft;
  the flared centering member is configured to be contained within the guide catheter lumen in a low-profile configuration for advancement through the lumen of the guide catheter and to expand to an expanded flared configuration when expelled from a distal end of the lumen of the guide catheter; and
  the guide wire is configured to be advanced through a lumen of the elongate shaft of the emboli-capturing centering device and to be ejected through the open distal end of the expanded and centered flared centering member in a position centered with respect to the orifice.

16. The system of claim 15, further comprising a covering material disposed over the flared distal portion of the centering member and configured to block passage of blood through the covering material and the distal portion of the centering member to center the axial lumen of the centering member with respect to the orifice.

17. The system of claim 16, wherein the filter material flares outwardly from a proximal end thereof, at the location at which the proximal end of the flared centering member is attached to the shaft, to a distal end thereof, and the covering material flares outwardly from the distal end of the filter material to the distal end of the centering member.

18. The system of claim 15, wherein the centering member is constructed from a flexible self-expanding material which can be collapsed for delivery.

19. A method for treating a human patient using a system that comprises: (a) an emboli-capturing centering device for centering a medical instrument in a conduit within a patient with respect to a jet flow of fluid flowing through a restricted orifice within the patient narrower than the conduit and distal to the emboli-capturing centering device, the emboli-capturing centering device comprising: (i) an elongate shaft; (ii) a flared centering member having an open distal end, a proximal end attached to the shaft, and an inner surface forming an axial lumen whose diameter decreases in a distal-to-proximal direction; and (iii) a flared filter material separate from the flared centering member and flared outwardly, in a distal direction, from the location at which the proximal end of the flared centering member is attached to the shaft; (b) a guide catheter having a lumen; and (c) a guide wire, wherein the flared centering member is configured to be contained within the guide catheter lumen in a low-profile configuration for advancement through the guide catheter lumen and to expand to an expanded configuration when expelled from a distal end of the guide catheter lumen, and wherein the guide wire is configured to be advanced through a lumen of the elongate shaft of the centering device and to be ejected through the open distal end of the flared centering member, the method comprising:
  inserting the guide catheter into a patient and directing the guide catheter to a target site within the patient wider than the restricted orifice;
  causing the flared centering member to emerge from a distal end of the guide catheter lumen and reconfigure from a low-profile configuration to an expanded configuration;
  allowing fluid to flow into the flared centering member and to contact the inner surface of the flared centering member to flow proximally along the decreasing diameter of the axial lumen to laterally shift the centering member to center the axial lumen of the centering member with respect to the orifice;
  causing the guidewire to emerge from a distal end of the lumen of the elongate shaft of the emboli-capturing centering device centered with respect to the orifice; and
  filtering blood passing through the filter material to capture emboli in the blood.

20. The method of claim 19, wherein the method is used to treat a stenotic aortic valve of the patient.

* * * * *

UNITED STATES PATENT AND TRADEMARK OFFICE
CERTIFICATE OF CORRECTION

Page 1 of 1

PATENT NO. : 11,166,803 B2
APPLICATION NO. : 15/945040
DATED : November 9, 2021
INVENTOR(S) : Roger W. McGowan et al.

It is certified that error appears in the above-identified patent and that said Letters Patent is hereby corrected as shown below:

On the Title Page

Item (73), ASSIGNEE: after "Boston Scientific Scimed, Inc., Maple Grove, MN (US)", insert --MAYO FOUNDATION FOR MEDICAL EDUCATION AND RESEARCH, Rochester, MN (US)--.

Signed and Sealed this
Twenty-fourth Day of September, 2024

Katherine Kelly Vidal
*Director of the United States Patent and Trademark Office*